United States Patent [19]

Böger et al.

[11] 4,223,027
[45] Sep. 16, 1980

[54] PHENYLFORAMIDINES AND PESTICIDAL METHODS USING SAME

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 3,315

[22] Filed: Jan. 15, 1979

Related U.S. Application Data

[63] Continuation of Ser. No. 853,924, Nov. 22, 1977, abandoned.

[30] Foreign Application Priority Data

Nov. 30, 1976 [CH] Switzerland ............. 15055/76
Jun. 16, 1977 [CH] Switzerland ............. 7405/77
Oct. 6, 1977 [CH] Switzerland ............. 12209/77

[51] Int. Cl.$^2$ ............. A01N 9/36; C07F 9/24
[52] U.S. Cl. ............. 424/211; 260/944
[58] Field of Search ............. 260/944; 424/211

[56] References Cited

U.S. PATENT DOCUMENTS

| | | | |
|---|---|---|---|
| 3,812,174 | 5/1974 | Brown et al. | 260/479 C |
| 3,887,619 | 6/1975 | Rizzo | 260/564 RF |
| 3,947,591 | 3/1976 | Rizzo et al. | 424/326 |
| 3,998,969 | 12/1976 | Rizzo | 424/324 |
| 4,081,536 | 3/1978 | Nelson | 424/211 |

*Primary Examiner*—Anton H. Sutto
*Attorney, Agent, or Firm*—John J. Maitner

[57] ABSTRACT

Phenylformamidines of the formula

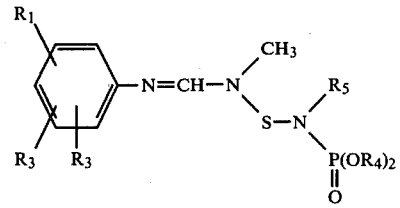

wherein $R_1$, $R_2$ and $R_3$ each represent hydrogen, $C_1$–$C_4$-alkyl, $C_1$–$C_4$-alkoxy or halogen, $R_4$ represents methyl or ethyl, and $R_5$ represents $C_1$–$C_8$-alkyl or $C_3$–$C_6$-cycloalkyl, processes for producing them, and their use for combating pests.

11 Claims, No Drawings

PHENYLFORAMIDINES AND PESTICIDA METHODS USING SAME

This is a continuation of application Ser. No. 853,924 filed on Nov. 22, 1977, now abandoned.

The present invention relates to phenylformamidines, to processes for producing them, and to their use for combating pests. The phenylformamidines have the formula

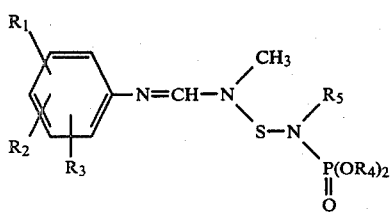

wherein
$R_1$, $R_2$ and $R_3$ each represent hydrogen, $C_1$–$C_4$-alkyl, $C_1$–$C_4$-alkoxy or halogen; $R_4$ represents methyl or ethyl; and $R_5$ represents $C_1$–$C_8$-alkyl or $C_3$–$C_6$-cycloalkyl. Halogen denotes herein fluorine, chlorine, bromine and/or iodine, especially chlorine and/or bromine. The alkyl and alkoxy groups denoted by $R_1$, $R_2$, $R_3$ and $R_5$ can be straight-chain or branched-chain. Examples of such groups are: methyl, methoxy, ethyl, ethoxy, propyl, isopropyl and n-, i-, sec.- or tert.-butyl. As cycloalkyl, $R_5$ is in particular cyclopropyl or cyclohexyl.

Phenylformamidines preferred by virtue of their effectiveness are those of the formula I wherein $R_1$, $R_2$ and $R_3$ each represent hydrogen, methyl, chlorine or bromine; $R_4$ represents methyl or ethyl; and $R_5$ represents methyl or cyclopropyl.

The phenylformamidines of the formula I can be produced by processes known per se, for example by reacting a compound of the formula

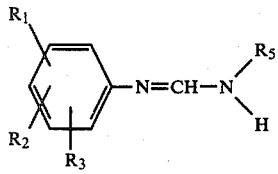

in the presence of an acid-binding agent, with a compound of the formula

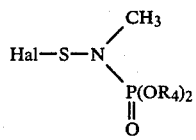

In the formulae II and III, $R_1$ to $R_5$ have the meanings given for the formula I, and "Hal" denotes a halogen atom, particularly chlorine or bromine. Suitable acid-binding agents are, in particular, tertiary amines such as trialkylamines and pyridine, also hydroxides, oxides, carbonates and bicarbonates of alkali metals and alkaline-earth metals, and also alkali metal alcoholates such as potassium-t.-butylate and sodium methylate. The process is performed at a reaction temperature of between $-20°$ and $+30°$ C., under normal or elevated pressure, and optionally in an inert solvent or diluent, or in an excess of the acid-binding agent used. Suitable solvents or diluents are, for example, ethers and ethereal compounds, such as diethyl ether ether, dipropyl ether, dioxane, dimethoxyethane and tetrahydrofuran; amides such as N,N-dialkylated carboxylic acid amides; aliphatic, aromatic as well as halogenated hydrocarbons, particularly benzene, toluene, xylenes, chloroform and chlorobenzene; nitriles such as acetonitrile; dimethylsulphoxide and ketones such as acetone and methyl ethyl ketone.

The starting materials of the formulae II and III are known or can be produced by methods analogous to known methods. The compounds of the formula I are suitable for combating various animal and plant pests. The compounds thus have nematocidal properties, and can be used for example for combating phytopathogenic nematodes. They are also suitable for combating viruses, bacteria and phytopathogenic fungi.

The compounds of the formula I are especially suitable for combating insects, and phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

The compounds of the formula I are suitable in particular for combating insects that damage plants, especially insects that damage plants by eating, in crops of ornamental plants and useful plants, particularly in cotton crops (e.g. against *Spodoptera littoralis* and *Heliothis virescens*) and in crops of vegetables (e.g. against *Leptinotarsa decemineata* and *Myzus persicae*). The active substances of the formula I also have a very favourable action against flies, such as *Musca domestica*, and against mosquito larvae.

The acaricidal and insecticidal action can be substantially broadened and adapted to suit given circumstances by the addition of other insecticides and/or acaricides. Suitable additives are, for example, organic phosphorus compounds; nitrophenols and derivatives thereof; formamidines; ureas; other pyrethrin-like compounds; as well as carbamates and chlorinated hydrocarbons. Compounds of the formula I are combined particularly advantageously with substances having an intensifying effect. Examples of such compounds are, inter alia: piperonyl butoxide, propynyl ethers, propynyl oximes, propynyl carbamates and propynyl phosphonates, 2-(3,4-methylenedioxyphenoxy)-3,6,9-trioxaundecane and S,S,S-tributylphosphorotrithioates.

The compounds of the formula I can be used on their own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays or solutions, the formulation of these being effected in a manner commonly known in the art. Also to be mentioned are cattle dips and spray races, in which aqueous preparations are used.

The compositions according to the invention are produced in a manner known per se by the intimate mixing and/or grinding of active substances of the formula I with suitable carriers, optionally with the addition of dispersing agents and solvents which are inert to the active substances. The active substances can be obtained and used in the following forms:

Solid Preparations: dusts, scattering agents or granules (coated, impregnated or homogeneous granules);

Liquid Preparations:
(a) water-dispersible concentrates of active substance: wettable powders, pastes or emulsions;
(b) solutions.

The content of active substance in the compositions described is between 0.1 and 95%. The active substances of the formula I can be formulated for example as follows:

Dusts

The following substances are used to produce (a) a 5% dust and (b) a 2% dust:

(a)

5 parts of active substance,
95 parts of talcum;

(b)

2 parts of active substance,
1 part of highly dispersed silicic acid,
97 parts of talcum.

The active substances are mixed and ground with the carriers.

Granulate

The following substances are used to produce a 5% granulate:

5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with the epichlorohydrin and dissolved with 6 parts of acetone; the polyethylene glycol and cetyl polyglycol ether are then added. The solution obtained is sprayed onto kaolin, and the acetone is evaporated off in vacuo.

Wettable powders

The following constituents are used to produce (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in the appropriate mills and rollers. There are obtained wettable powders which can be diluted with water to give suspensions of the desired concentration.

Emulsifiable concentrate

The following substances are used to produce (a) a 10%, (b) a 25%, and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;

(c)

50 parts of active substance,
4.2 parts of tributylphenol-polyglycol ether,
5.8 parts of calcium-dodecylbenzenesulphonate,
20 parts of cyclohexanone,
20 parts of xylene.

Emulsions of the desired concentration can be prepared from these concentrates by dilution with water.

Spray

The following constituents are used to produce (a) a 5% spray and (b) a 95% spray:

(a)

5 parts of active substance,
1 part of epichlorohydrin,
94 parts of ligroin (boiling limits 160°–190° C.), (b)

95 parts of active substance,
5 parts of epichlorohydrin.

The invention is further illustrated by the following Examples.

EXAMPLE 1

Production of 1-(2-methyl-4-chlorophenyl)-3,5-dimethyl-1,3,5-triaza-4-sulpha-5-0,0-dimethyl-phosphonyl-hex-1-ene 9.5 g of triethylamine is added to a solution of 16.6 g of N-methyl-N'-(4-chloro-2-methylphenyl)-formamidine in 100 ml of methylene chloride. There is then slowly added dropwise at 0° C. with continuous stirring 18.5 g of the compound of the formula

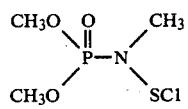

The mixture is stirred for a further half hour without cooling, and 100 ml of water is thereupon added. The methylene chloride solution is dried and then evaporated off under high vacuum to yield the compound of the formula

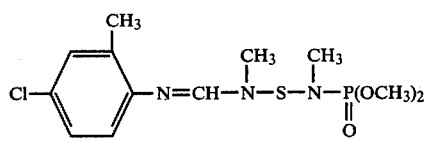

as yellow oil having a refractive index of $n_D^{20°} = 1.5624$.

The following compounds are produced in an analogous manner:

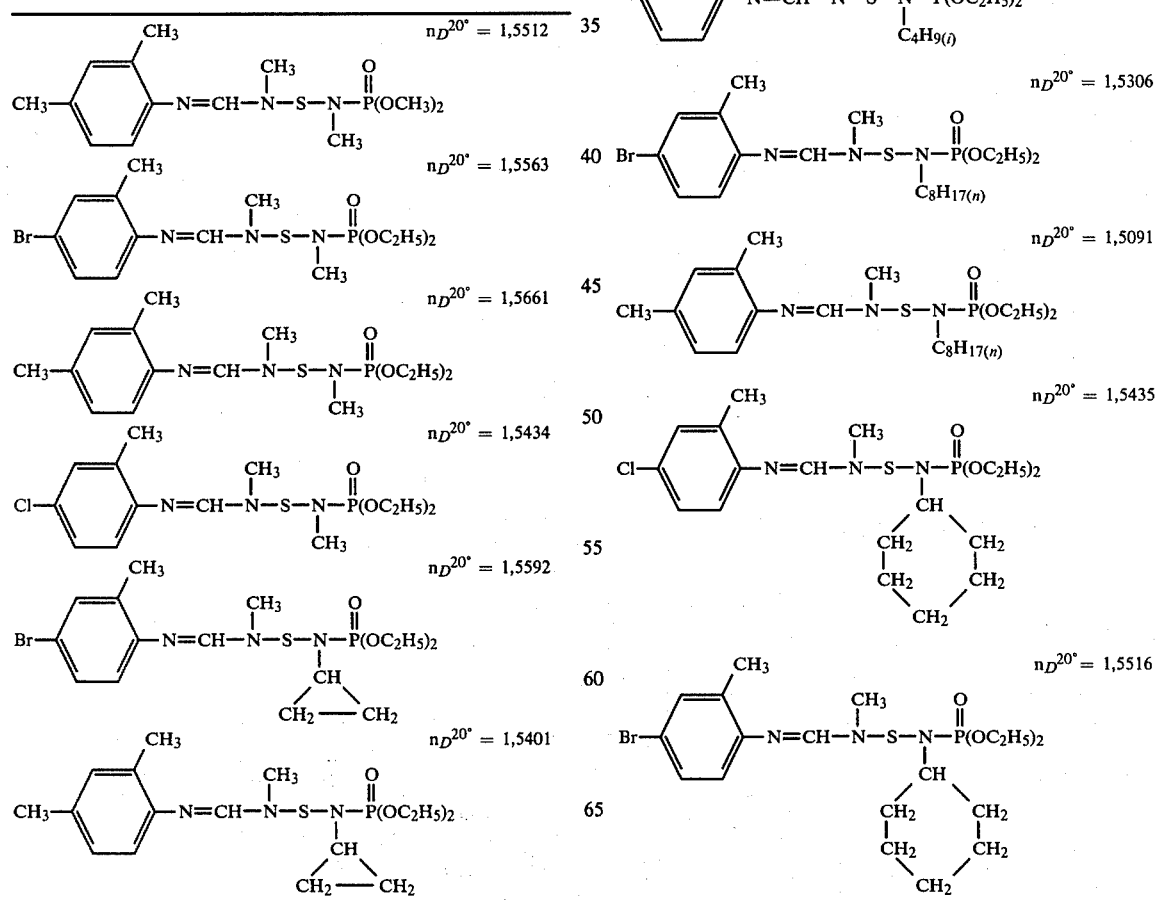

-continued $$CH_3\text{-}\underset{CH_3}{\underset{|}{\bigcirc}}\text{-}N=CH-\underset{|}{\overset{CH_3}{N}}-S-\underset{|}{\overset{}{N}}-\overset{O}{\overset{\|}{P}}(OC_2H_5)_2 \quad n_D^{20°} = 1.5390$$

with CH group bearing $-CH_2-CH_2-CH_2-CH_2-CH_2-$ (cyclohexyl ring)

$$CH_3O\text{-}\underset{CH_3}{\underset{|}{\bigcirc}}\text{-}N=CH-\underset{|}{\overset{CH_3}{N}}-S-\underset{|}{\overset{}{N}}-\overset{O}{\overset{\|}{P}}-(OC_2H_5)_2 \quad n_D^{20°} = 1.5387$$

with CH group bearing $-CH_2-CH_2-CH_2-CH_2-CH_2-$ (cyclohexyl ring)

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of Spodoptera littoralis in the $L_3$-stage and of Heliothis virescens in the $L_3$-stage were placed onto the cotton plants. The test was carried out at 24° C. with 60% relative humidity.

Compounds according to Example 1 exhibited in the above test a good insecticidal stomach-poison action against larvae of *Spodoptera littoralis* and *Heliothis virescens*.

(B) Systemic insecticidal action

In order to determine the systemic action, rooted bean plants (Vicia faba) were placed into a 0.01% aqueous solution of the active substance (obtained from a 10% emulsifiable concentrate). After 24 hours, bean aphids (*Aphis fabae*) were placed onto the parts of the plants that had been above the soil. By means of a special device, the bean aphids were protected from the effects of contact and of gas. The test was carried out at 24° C. with 70% relative humidity.

Compounds according to Example 1 exhibited in the above test a systemic insecticidal action against *Aphis fabae*.

EXAMPLE 3

Action against Chilo suppressalis

Rice plants of the variety Caloro were planted six plants per pot in plastic pots having an upper diameter of 17 cm, and grown to a height of about 60 cm. Infestation with *Chilo suppressalis* larvae ($L_1$; 3–4 mm long) was carried out 2 days after application of the active substance in granular form (amount applied = 8 kg of active substance per hectare) to the paddy water. An evaluation of the insecticidal action was made 10 days after application of the granules.

Compounds according to Example 1 exhibited in the above test a good action against *Chilo suppressalis*.

EXAMPLE 4

Acaricidal action

*Phaseolus vulgaris* plants were infected, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 and 7 days, by examination under a binocular microscope, of the living and of the dead larvae, adults and eggs, and the results were expressed as percentages. The treated plants were kept during the "holding time" in greenhouse compartments at 25° C.

Compounds according to Example 1 exhibited in the above test a good action against adults, larvae and eggs of *Tetranychus urticae*.

EXAMPLE 5

Action against soil nematodes

In order to test their action against soil nematodes, the active substances were added to soil infested with root-gall nematodes (*Meloidogyne arenaria*), and intimately mixed with the soil. In one test series, tomato seedlings were planted immediately after preparation of the soil in this manner, and in the other test series tomatoes were sown after a waiting time of 8 days. An assessment of the nematocidal action was made by counting the galls present on the roots 28 days after planting and sowing, respectively.

Active substances according to Example 1 exhibited in this test a good action against *Meloidogyne arenaria*.

EXAMPLE 6

Action against ticks

(A) Rhipicephalus bursa

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(B) Boophilus microplus (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 7

Action against Erysiphe graminis on Hordeum vulgare

Barley plants about 8 cm in height were sprayed with a spray liquor prepared from wettable powder of the active substance (0.05% of active substance). After 48 hours, the treated plants were dusted with conidia of the fungus. The infested barley plants were placed in a greenhouse at about 22° C. and the fungus infestation was assessed after 10 days.

Compound according to Example 1 were effective in this test against *Erysiphe graminis*.

We claim:

1. A phenylformamidine of the formula

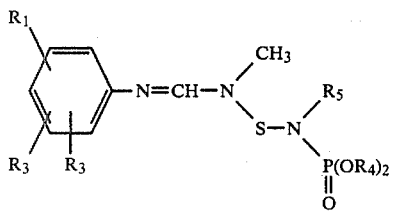

wherein
R₁ is in the 2-position,
R₁ and R₂ each represent $C_1$-$C_4$-alkyl, $C_1$-$C_4$-alkoxy or halogen;
R₃ represents hydrogen;
R₄ represents methyl or ethyl; and
R₅ represents $C_1$-$C_8$-alkyl or $C_3$-$C_6$-cycloalkyl.

2. A phenylformamidine according to claim 1, wherein
R₁ and R₂ each represent methyl chlorine or bromine;
R₄ represents methyl or ethyl; and
R₅ represents methyl or cyclopropyl.

3. The phenylformamidine according to claim 2, of the formula:

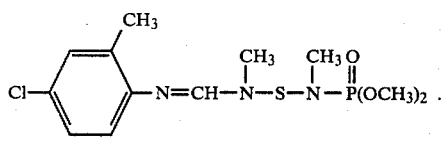

4. The phenylformamidine according to claim 2, of the formula:

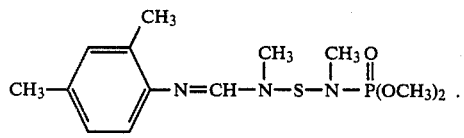

5. The phenylformamidine according to claim 2, of the formula:

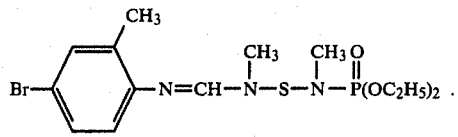

6. The phenylformamidine according to claim 2, of the formula:

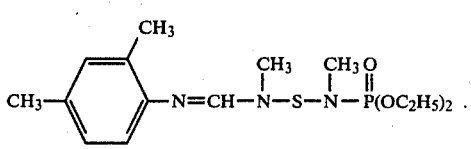

7. The phenylformamidine according to claim 2, of the formula:

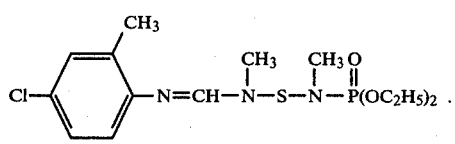

8. The phenylformamidine according to claim 2, of the formula:

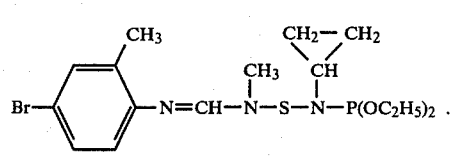

9. The phenylformamidine according to claim 2, of the formula

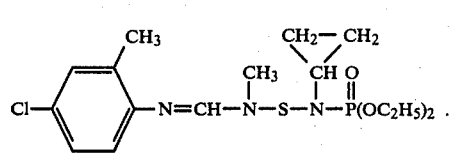

10. An insecticidal and acaricidal composition comprising an insecticidally or acaricidally effective amount of a compound according to claim 1, together with a suitable carrier therefor.

11. A method for combating insects and acarids which comprises applying to the locus thereof an insecticidally or acaricidally effective amount of a compound according to claim 1.

* * * * *